US005798250A

United States Patent [19]
Zeytinoglu

[11] Patent Number: 5,798,250
[45] Date of Patent: Aug. 25, 1998

[54] FACILITATING HEPATITUS VIRUS INFECTION IN CELL CULTURE USING A MEMBRANE STRESSOR

[75] Inventor: Füsûn Zeytinoglu, Del Mar, Calif.

[73] Assignee: ICN Pharmaceuticals, Inc.

[21] Appl. No.: 632,636

[22] Filed: Apr. 15, 1996

[51] Int. Cl.$^6$ ..................................... C12N 7/00
[52] U.S. Cl. .................. 435/235.1; 435/239; 435/325
[58] Field of Search ........................ 435/235.1, 239, 435/325

[56] References Cited

U.S. PATENT DOCUMENTS 5,264,618  11/1993  Felgner et al. .

5,578,475  11/1996  Jessee .

*Primary Examiner*—Leon B. Lankford, Jr.
*Attorney, Agent, or Firm*—Crockett & Fish

[57] ABSTRACT

Methods and compositions are provided for infecting cells with virus. Specific embodiments involved stressing the cellular membranes with chemical, electrical or mechanical means, such as by incubating the cells in DOTAP or Transfectam™. Other embodiments involve impregnating carriers with virus for use in research a suitable carrier such as a polymer or nanoparticle.

4 Claims, No Drawings

1

FACILITATING HEPATITUS VIRUS INFECTION IN CELL CULTURE USING A MEMBRANE STRESSOR

I. FIELD OF THE INVENTION

The field of the invention is virology.

II. BACKGROUND OF THE INVENTION

Research into the etiology and treatment of numerous viral diseases has long suffered from a paucity of successful in vitro models. With respect to Hepatitis C Virus (HCV), for example, one of the major impediments to the structural analysis of the HCV genome and genetic analysis of viral replication has been the lack of a reliable cell culture model. Yoo, Young J., "Transfection of a Differentiated Human Hepatoma Cell Line (Huh7) with In Vitro-Transcribed Hepatitis C Virus (HCV) RNA and Establishment of a Long-Term Culture Persistently Infected with HCV", *J. of Virology*, 69:1, 32–38 (1995); Lanford, R. E. et al., "Demonstration of in vitro infection of chimpanzee hepatocyte: hepatitis C virus using strtand-specific RT/PCR", *Virology*, 202: 606–14 (1994).

Previous attempts to infect cells with the hepatitis C virus have achieved only sporadic success, and only through the use of particularly susceptible cell lines. See, e.g. Nobuyuki, Kato et al., "Susceptibility of Human T-Lymphotropic Virus Type I Infected Cell Line MT-2 to Hepatitis C Virus Infection", *Biochem. and Biophys. Res. Comm.*, 206:3, 863–869 (1995). Shimizu, Yohko. K., et al., "Evidence for In Vitro Replication of Hepatitis C Virus Genome In A Human T-Cell Line", *Proc. Natl. Acad. Sci.*, 89, 5477–5481 (1992).

It is known that certain agents such as UV light and heat shock can induce expression of virus in infected cells, but the use of such agents has not been generalized to infection of non-infected cells. See, e.g. Stanley, S. K. et al, "Induction of expression of human immunodeficiency virus in a chronically infected promonocytic cell line by ultraviolet irradiation", *AIDS Res. Hum. Retroviruses*, 5, 375–84 (1989); Stanley, S. K., "Heat shcok inductino of HIV production from chronically infected promonocytic and T cell lines", *J. Immunol.*, 145, 1120–6 (1990).

Because of the many difficulties attending transfection of culture cells with intact virus (virion), much of the work has focused on transfecting cells with viral nucleoid (genetic material). Experimental work has been done, for example, on transferring DNA or RNA directly into cells in culture using calcium phosphate or other divalent cations, polycations, liposomes, micro-injection and electroporation. One of the more promising agents for achieving transfection of cells in this manner is the transfection reagent DOTAP, N-[1-(2,3-Dioleoylocy)propyl]-N,N,N-trimethylammonium methylsulfate. To my knowledge, however, use of DOTAP to transfect cells with naked nuclear material has not resulted in efficient and reliable in vitro infection models, nor has DOTAP been used to infect cells with intact virus.

In addition to the need for reliable in vitro infection models, there is a need for models which harbor virus outside a living cell. Such models could be used, for example, for rapid screening of anti-viral agents, target cell populations, and therapeutic agents, and for elucidation of the mechanisms of action of viral infection.

III. SUMMARY OF THE INVENTION

The present invention provides novel methods and compositions for utilizing virus, including chemical, electrical and mechanical means of artificially stressing cells in vitro to make them more susceptible to viral infection, and methods and compositions for harboring virus for use in research. One preferred embodiment includes association of intact virus with cationic liposomes to infect cells in culture. Other preferred embodiments include entrapping virus on or within a suitable carrier such as a polymer or nanoparticle.

IV. DETAILED DESCRIPTION OF SPECIFIC EMBODIMENTS

Infection of Cells

It is thought that infection of cells according to the present invention takes place pursuant to disruption of the cellular membrane. Suitable disruption requires that the cell survive the disruption, and can occur as a result of virtually any means, all of which for purposes of this application are segregated into chemical, electrical and mechanical means. Chemical disruption may occur, for example, through manipulation of various factors in the ambient media including ionic balance, pH, and osmolarity (such as use of distilled water), and addition of chemicals such as iron to the cell medium. Substances which alter the membrane can also be used, such as those which cause poration, enhance permeability, or encourage transport through existing pores. Electrical disruption may occur, for example, through the application of electric current, or in the presence of sufficient voltage gradients or local static charges. Mechanical disruption may occur, for example, through the use of sonic waves, perforating guns and temperature effects.

Of course, since virus itself gains entry into a cell by disrupting the cellular membrane, the inventions herein are directed to artificial disruption, i.e. disruption other than that which would normally occur by application of the infecting virus. Artificial disruption also excludes effects occurring naturally in biological systems, such as exposure of an organism to sunlight, dehydration or sleep deprivation, or reduction in an organism's immological defences through prior infections, malnutrition, and so forth.

In a preferred embodiment, cells are infected with hepatitis C virus using DOTAP or Transfectam™ according to a series of exemplary experiments performed by Donald F. Smee, Ph.D. at Utah State University, Logan, Utah. In those experiments, IM-9, and SC-1) and one T-cell line (MOLT-4) were purchased from the American Type Culture Collection, Rockville, Md. The cells were grown in suspension in RPMI-1640 medium supplemented with 10% (IM-9, SC-1, or MOLT-4 cells) or 20% (Daudi cells) fetal bovine serum. About $10^{-4}$ of each of these cells was seeded into wells of 96-well plates, and then exposed to the above media containing 20% human serum which was Hepatitis C virus infected at $5-9 \times 10^5$ viral RNA genomes per ml. The serum was provided by Dr. Ann Warford of Stanford Health Services. To study different infection conditions, some of the cells were exposed also to one of the following: 1% DMSO; 4% PEG 8000; 1% DMSO+4% PEG 8000; DOTAP (Boehringer Mannheim); or Transfectam™ (Promega), each at 10 µg/ml. These media were left on the cells overnight, then the medium was changed to normal growth medium thereafter. Every 2–3 days part of the medium was discarded and replaced with fresh growth medium. As the cells multiplied they were transferred to 24 well plates.

Detection of HCV infection was accomplished by using an HCV capsid antibody from Virostat, Inc, Portland, Me., followed by a goat anti-mouse antibody (Organon Technica, West Chester, Pa.). After 9–14 days the cells were fixed with methanol, stained, and evaluated for fluorescence. The table below illustrates the results. Good infection in culturable cell lines (reproducable to at least one order of magnitude over control levels of infection) was achieved with DOTAP and Transfectam™, but not with the other reagents. The extent of intracellular virus replication as quantified by polymerase chain reaction, and transmissibility of the infection from these cells to uninfected cells will be determined in later experiments.

TABLE 1. Infection of cells with HCV.

| Cell Line | Reagent | % Infected Cells |
|---|---|---|
| IM-9 | none | 1 |
| IM-9 | DMSO | 1 |
| IM-9 | PEG | 1 |
| IM-9 | DMSO/PEG | 1 |
| IM-9 | DOTAP | 50 |
| IM-9 | Transfectam ™ | 50 |
| MOLT-4 | none | 1 |
| MOLT-4 | DMSO | 1 |
| MOLT-4 | PEG | 1 |
| MOLT-4 | DMSO/PEG | 1 |
| MOLT-4 | DOTAP | 25 |
| MOLT-4 | Transfectam ™ | 10 |
| DAUDI | none | 1 |
| DAUDI | DMSO | 1 |
| DAUDI | PEG | 1 |
| DAUDI | DMSO/PEG | 1 |
| DAUDI | DOTAP | 25–50 |
| DAUDI | Transfectam ™ | 10 |
| SC-1 | none | 1 |
| SC-1 | DMSO | 1 |
| SC-1 | PEG | 1 |
| SC-1 | DMSO/PEG | 1 |
| SC-1 | DOTAP | 25 |
| SC-1 | Transfectam ™ | 10 |

Of course, while specific procedures, cell lines, virus, media and other reagents were utilized in these particular experiments, there are many variations which would also be effective. The cells to be infected, for example, could be human or non-human or some combination, they could comprise one or more different cell types including hepatocytes, neural cells and others, and they could be infected at various different stages of maturity and cell cycle. Any virus could be used, including DNA or RNA virus. The cells to be infected could be placed in any supportive media, or multiple media, which may itself or in combination with other artificial stressors sufficiently stress the cellular membranes to promote infection. The order of events is also subject to change. For example, the virus may be added to the media before or after adding the DOTAP or Transfectam™, or in some other manner stressing the cellular membranes. As another example, the length of time with which the cells are stressed can be more or less than that used in the experiments reported herein. Still further, it is not necessary to practice the invention that all of the cells sought to be infected actually become infected. Some of the cells may be killed or rendered inactive, some may remain uninfected, and some may become infected but may be unable to propagate further infection.

It is also important to recognize that while the present theoretical foundation involves artificially stressing of the cell membrane, the scope and interpretation of the appended claims is not dependent upon the extent to which the theoretical foundation is found to be entirely accurate.

Virus Impregnated Carriers

In another aspect of the invention, a carrier can be impregnated with virus. Suitable means of impregnation include adsorbtion, absorption, covalent or ionic linkage, and other means, as long as the virus can be recovered from the carrier in a viable state. Carriers suitable for virus impregnation include polymers and especially dendromers, starch and carbohydrate complexes including cyclodextrins and matregels, and protein structures including polylycine.

Use of Models

To one skilled in the art, use of in vitro models follows directly from the knowledge that cells can be reliably and reproducibly infected according to the disclosure herein. Viral impregnated carriers, such as nanoparticles and partisomes, for example, may be used in experiments to enhance specificity and reproducibility. The carrier may be designed to have zero order kinetics (carrier alone), and can be designed to achieve measured release of the virus through degradation of the carrier, either intra- or extra-cellularly. Embodiments of viral impregnated carrier may have particular shapes and/or sizes to study various aspects of active and/or passive membrane transport.

Virus impregnated carriers can also be transplanted into target organs or tissues for in vivo study, where selection of carrier can be used to target specific organs and tissues. For example, delivery to the liver can be enhanced by using carriers which target asialoglycoprotein or orosomucoid receptors. Thus, the invention contemplates in vitro, in vitro, and ex vivo models.

Virus impregnated carrier may also be used to screen new and old pharmaceutical compositions, for example, by facilitating testing of an anti-viral agent directly on the virus, or on target cells which would otherwise become infected, or infect other cells at a predictable rate. In a similar manner the kinetics of viral clearance and dose response (either site specific or virus specific) can be studied. Still further, suitable models as contemplated herein may be used to screen the following: (a) multiple target cells; (b) the effects of specific conditions which may affect gene induction; (c) sequential viral infection; (d) inhibition of viral propagation; (e) virastatic effects; (f) lytic effects; (g) time course of viral infection; (h) kinetics of viral clearance, and so forth.

Technologies such as display PCR may be used in conjunction with models contemplated herein to elucidate the mechanism(s) of viral infection by identifying genes that are under- or overexpressed in, for example, (a) control cells; (b) cells infected with virus; (c) cells resistant to virus; (d) cells which have cleared the virus; (e) and cells which sequester the virus.

The rational design and screening of pharmaceuticals will be greatly facilitated by use of the models contemplated herein. One particular path of inquiry, for example, could be differentiating cells which are susceptible to infection from those which are resistant to infection.

EQUIVALENTS

The foregoing written specification is considered to be sufficient to enable one skilled in the art to practice the invention. Indeed, various modifications of the above-described makes for carrying out the invention which are obvious to those skilled in the field of virology or related fields are intended to be within the scope of the following claims.

What is claimed is:

1. A method of infecting cells with Hepatitis C virus comprising:

providing cells in a culture medium;

exposing the cells to the virus; and artificially exposing the cells to a sufficient amount of membrane stressor comprising at least one of DOTAP (N-[1-(2,3-Dioeoylocy)propyl]-N,N,N-trimethylammonium methylsulfate and Transfectam™ (dioctadecylamidoglcyl spermine) to facilitate infection.

2. The method of claim 1 wherein facilitation of infection occurs when the percent of infected cells is at least one order of magnitude over that achieved without the stressor.

3. The method of claim 1 wherein facilitation of infection occurs when the percent of infected cells is at least ten times that achieved without the stressor.

4. A method of infecting cells with Hepatitis virus comprising:

providing cells in a culture medium;

exposing the cells to the virus; and artificially exposing the cells to a sufficient amount of a membrane stressor wherein the membrane stressor is selected from at least one of DOTAP (N-[1-(2,3-Dioeoylocy)propyl]-N,N,N-trimethylammonium methylsulfate) and Transfectam™ (dioctadecylamidoglcyl spermine) to facilitate infection.

* * * * *